United States Patent

Nakamura et al.

[11] Patent Number: 6,015,840
[45] Date of Patent: Jan. 18, 2000

[54] PROCESS FOR PRODUCING EMULSIFIERS, AND EMULSIFIED COMPOSITIONS

[75] Inventors: Akihiro Nakamura; Masayoshi Kato; Taro Takahashi; Hirokazu Maeda, all of Tsukuba-gun, Japan

[73] Assignee: Fuji Oil Co., Ltd., Osaka, Japan

[21] Appl. No.: 09/011,374

[22] PCT Filed: Jun. 6, 1997

[86] PCT No.: PCT/JP97/01921

§ 371 Date: Feb. 4, 1998

§ 102(e) Date: Feb. 4, 1998

[87] PCT Pub. No.: WO97/46312

PCT Pub. Date: Dec. 11, 1997

[30] Foreign Application Priority Data

Jun. 7, 1996 [JP] Japan .................................. 8-145823

[51] Int. Cl.[7] .............................. B01F 3/00; A23L 1/222; D21C 1/00

[52] U.S. Cl. ......................... 516/270; 426/654; 435/277

[58] Field of Search .......................... 426/654; 252/312; 435/277; 516/270

[56] References Cited

U.S. PATENT DOCUMENTS

| | | | |
|---|---|---|---|
| 5,008,254 | 4/1991 | Weibel | 514/57 |
| 5,200,215 | 4/1993 | Slade et al. | 426/18 |
| 5,213,968 | 5/1993 | Castle et al. | 435/68.1 |
| 5,342,641 | 8/1994 | Masutake et al. | 426/549 |
| 5,501,860 | 3/1996 | Maeda et al. | 424/464 |
| 5,538,884 | 7/1996 | Dorreich et al. | 435/200 |
| 5,700,397 | 12/1997 | Maeda et al. | 252/312 |

*Primary Examiner*—D. Gabrielle Brouillette
*Assistant Examiner*—Monique T. Cole
*Attorney, Agent, or Firm*—Wallenstein & Wagner, Ltd.

[57] ABSTRACT

A process for producing an emulsifier which comprises hydrolysis of water-soluble hemicellulose with purified rhamnogalacturonase, and emulsified compositions prepared using the emulsifier.

2 Claims, 4 Drawing Sheets

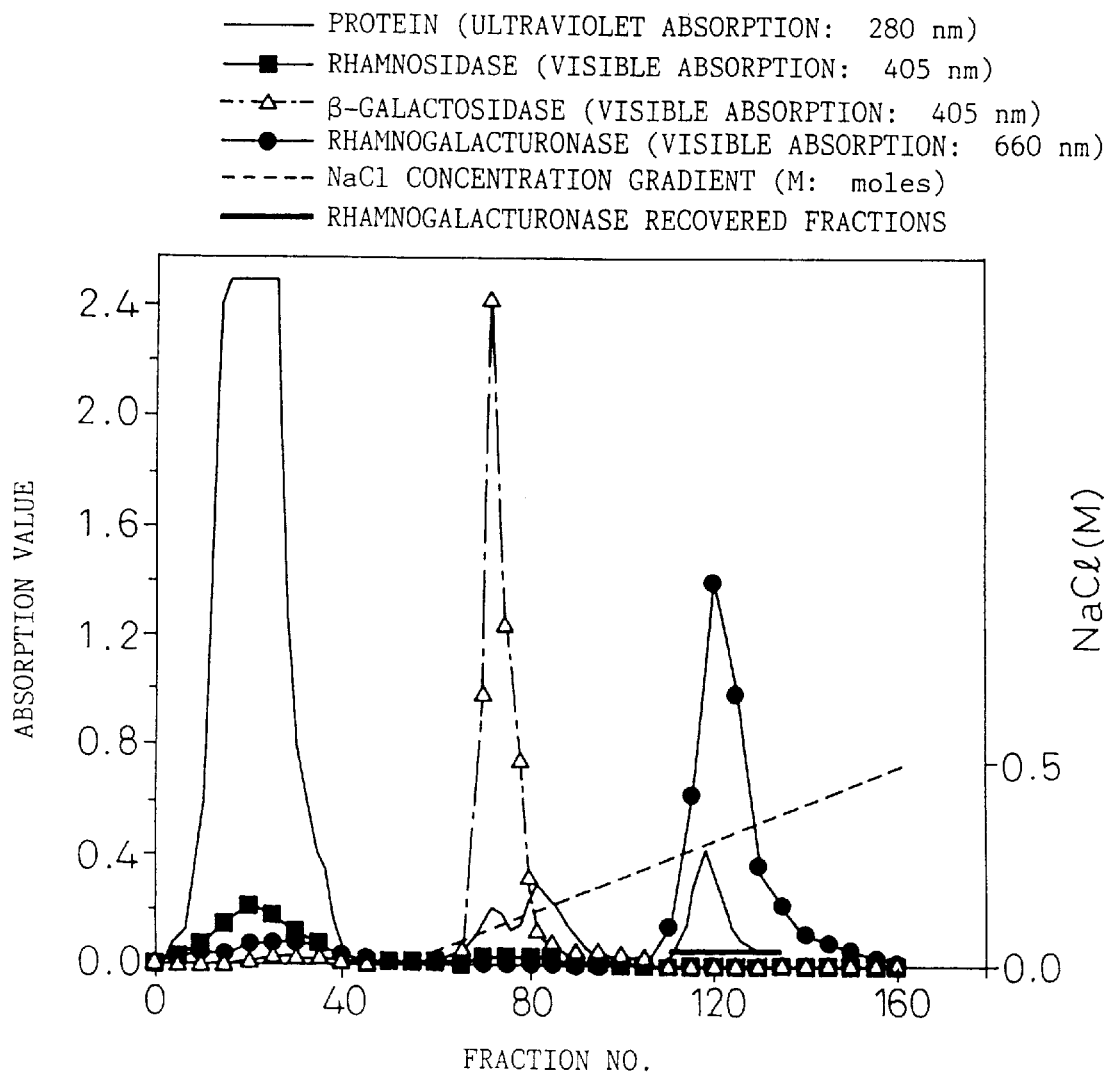

PROCESS FOR PRODUCING EMULSIFIERS, AND EMULSIFIED COMPOSITIONS

TECHNICAL FIELD

The present invention relates to a process for producing emulsifiers and to emulsified compositions obtained using the emulsifiers.

BACKGROUND ART

Emulsifiers can be largely classified into low molecular emulsifiers and high molecular emulsifiers. The low molecular emulsifiers are the so-called surfactants, and include fatty acid soaps, glycerin esters and sugar esters. High molecular emulsifiers include natural substances such as gum arabic and other rubbers and casein, as well as synthetic products such as acrylic acid salts and polyvinyl alcohols.

These emulsifiers are used in appropriate admixture depending on the purpose of use, but low molecular emulsifiers generally have the disadvantage of susceptibility to pH changes and loss of an emulsifying property as a result of changes in concentration resulting from salt addition or dilution.

Because the natural high molecular substance gum arabic must be used at a high concentration to achieve stable emulsions, while its supply volume is highly dependent on the weather conditions in the producing nation and its cost is highly variable, there has been a need in recent years for natural high molecular emulsifiers which can be provided in stable supply. On the other hand, synthetic products such as polyacrylic acid salts and polyvinyl alcohols are often limited in their uses because of problems with their emulsifying properties. An additional problem of natural high molecular emulsifiers is that they generally have high viscosity even at low concentrations, and thus their handleability is poor during the preparation of emulsions.

As mentioned above, emulsifiers employed for a variety of uses must provide emulsions which maintain a stable emulsified state over long periods, and when used in foods they must provide an appropriate taste and texture.

For example, although gum arabic is widely used as an emulsifier for emulsified aromatics, it has the problems mentioned earlier. Also, xanthan gum is widely used as an emulsifier for mayonnaise and dressings, but it gives highly viscous products and does not always provide the desired texture. In addition, casein used in creams such as coffee cream is not always satisfactory because of its high susceptibility to pH changes and the breakdown of its emulsions upon dilution.

DISCLOSURE OF THE INVENTION

As a result of diligent research in light of these facts, the present inventors have found that emulsified compositions with high emulsifying properties, storage stability, pH resistance, salt resistance and temperature resistance can be obtained by using as emulsifiers a decomposition product from the decomposition of water-soluble hemicellulose with a specific enzyme. The present invention is based upon this finding.

Specifically, the present invention provides a process, for producing emulsifiers, which comprises hydrolysis of water-soluble hemicellulose with purified rhamnogalacturonase, and emulsified compositions obtained us uch emulsifiers.

DESCRIPTION OF THE DRAWINGS

FIG. 4 is a chromatogram from affinity chromatography of AC:soybean pectin-derived rhamnogalacturonan using crosslinked rhamnogalacturonan (CLRG: Cross-Linked Rhamnogalacturonan) prepared by crosslinking.

BEST MODE FOR CARRYING OUT THE INVENTION

Figure 1:
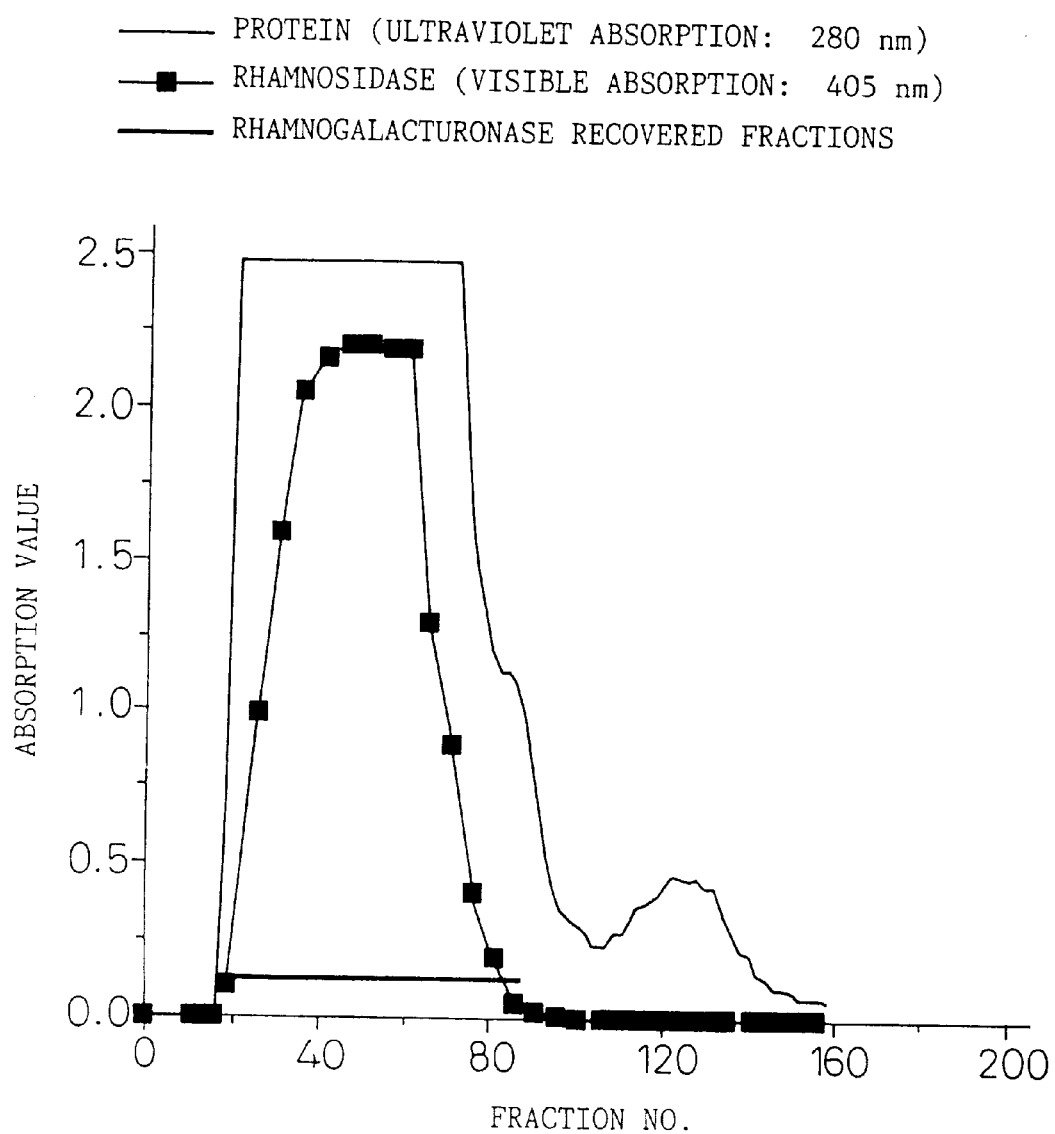
FIG. 1 is a gel chromatogram from gel filtration chromatography of a rhamnogalacturonase crude enzyme solution using GFC:TSKgel HW-50S (Super fine) (gel filtration chromatography filler, product of Toso Co.).

The water-soluble hemicellulose used as the starting material according to the invention can be of any molecular weight, but preferably has an average molecular weight of a few thousand to a few million, and specifically 5000 to one million. If the molecular weight is too large the viscosity will increase, thus lowering the handleability. The average molecular weight of the water-soluble hemicellulose is the value determined by the limiting viscosity method wherein the viscosity of a 0.1 M $NaNO_3$ solution is measured using standard pullulan (product of Showa Denko, KK.) as the standard substance. Measurement of uronic acid was carried out by the Blumenkrantz method and measurement of neutral sugars was carried out by the GLC method after alditol acetation.

The water-soluble hemicellulose is either obtained by water extraction from a hemicellulose-containing starting material or, if necessary, heat elution under acid or alkali conditions, or it may be eluted by decomposition with an enzyme. The following is an example of a method for producing water-soluble hemicellulose.

First, suitable starting materials to be used include the husks of oily seeds of soybean, palm, coconut, corn or cottonseed with the oil and protein removed, and lees from grains such as rice or wheat and roots such as beets with the starch or sugar removed; particularly preferred is soybean, especially as derived from the cotyledon, and okara (bean-curd refuse) may also be used as a by-product from preparation of tofu (bean curd) and soybean milk or separated soybean protein.

These starting materials may be subjected to heat decomposition at a temperature preferably of from 80° C. to 130° C., and more preferably from 100° C. to 130° C., under either acidic or alkali conditions but preferably at a pH near the isoelectric point of each protein, and after fractionation of the water-soluble fraction, it may be dried directly or subjected to activated carbon treatment, resin adsorption treatment or ethanol precipitation to remove the hydrophobic substances or low molecular substances, and then dried to yield the water-soluble hemicellulose.

Water-soluble hemicellulose is a polysaccharide containing galactose, arabinose, xylose, rhamnose, fucose, glucose and galacturonic acid as constituent saccharides. A detailed analysis of the constituents of water-soluble hemicellulose as obtained by hydrolysis may be found in Japanese Unexamined Patent Publication No. 4-325058.

Galacturonic acid contains 2 types of carboxylic groups, one in a methyl ester bond and-another as a free group, and it is preferably demethoxylated, from which viewpoint the esterification degree is preferably no greater than 50%, and more preferably no greater than 20%.

The purified rhamnogalacturonase used according to the invention is an enzyme which selectively degrades rhamnogalacturonan, and it is preferably in as pure a state as possible. Purified rhamnogalacturonase according to the invention is rhamnogalacturonase which exhibits a superior activity value compared to the activity value of other enzymes such as β-galactosidase, β-glucosidase or α-arabinosidase, exhibiting a superior activity value by at least a factor of 10, and preferably a factor of 100. The purity of the rhamnogalacturonase is such as to give an enzyme activity value of at least 20 units/mg, and preferably at least 25 units/mg of the protein.

The source of the rhamnogalacturonase may be, for example, *Aspergillus aculeatus*, of which the enzyme preparation Pectinex Ultra SP-L (crude enzyme) commercially available from Novo Nordisk Japan Co. is especially suitable, and this crude enzyme may be purified to obtain rhamnogalacturonase of a grade usable for the invention. A detailed explanation regarding this enzyme may be found in Japanese Patent Internal Publication No. 6-506831.

The viscosity of the enzyme-decomposed water-soluble hemicellulose solution is, in the case of a 10% aqueous solution, preferably no greater than 50 centipoise, more preferably no greater than 30 centipoise and most preferably no greater than 15 centipoise. The low viscosity of such aqueous solutions of water-soluble hemicellulose results in superior handleability during preparation of emulsions, as compared to non-enzyme-decomposed water-soluble hemicellulose.

According to the invention, the water-soluble hemicellulose obtained by hydrolysis with purified rhamnogalacturonase may be used alone as an emulsifier, but it may also be used in combination with existing emulsifiers to Compensate for their drawbacks.

As existing low molecular emulsifiers there may be mentioned various anionic surfactants represented by fatty acid soaps, cationic surfactants such as quaternary ammonium salts, nonionic surfactants such as glycerin fatty acid esters and sugar esters, amphoteric surfactants such as lecithin, and natural surfactants such as saponin.

As existing high molecular emulsifiers there may be mentioned natural emulsifiers, such as glue plant (funori), agar, carrageenan, furcellaran, tamarind seed polysaccharides, angelica gum, gum karaya, pectin, xanthan gum, sodium alginate, tragacanth gum, guar gum, locust bean gum, pullulan, jellan gum, gum arabic, gelatin, whey and other albumins, casein sodium and various starches. Also, as examples of semi-synthetic sizing agents there may be mentioned carboxymethyl cellulose (CMC), methyl cellulose (MC), hydroxyethyl cellulose (HEC), propylene glycol alginate and processed starches, typically soluble starches, and as examples of synthetic sizing agents there may be mentioned polyvinyl alcohols and sodium polyacrylate. As examples of existing dispersing agents there may be mentioned thickeners such as high methoxyl pectin (HM pectin), carboxymethyl cellulose sodium and propylene glycol alginate.

According to the invention, when the emulsifier obtained by hydrolysis of water-soluble hemicellulose with purified rhamnogalacturonase is used for production of aromatic emulsions, the emulsified products have greater stability including heat resistance, salt resistance and alcohol resistance, as well as better suspension stability, than that achieved by using gum arabic or processed starch, and when used for mayonnaise or dressings, fresher mayonnaise and dressings with much lower viscosity can be obtained than by using xanthan gum or starches. In addition, the emulsifiers can be used in creams, such as coffee whiteners, to give more stable creams which are less susceptible to demulsification by pH changes and dilution.

In addition, the stability may be further improved by addition of typical sugars such as sucrose and starch syrup, or polyhydric alcohols such as glycerin, D-sorbitol and propylene glycol, as well as organic acids such as lactic acid, table vinegar, citric acid and malic acid, to the aqueous phase. Other additives, for example anti-fading agents and preservatives such as L-ascorbic acid and its derivatives or aminocarbonyl reaction products, may also be added.

Other uses for emulsifiers obtained by hydrolysis of water-soluble hemicellulose with purified rhamnogalacturonase according to the invention include, in addition to the food products mentioned above, their uses as various types of emulsifiers and dispersants for cosmetic and pharmaceutical creams, such as hand creams and ointments. They may also be used in agricultural chemicals, such as oil-in-water emulsion-type insecticides and herbicides, to provide extended stability for emulsions and dispersions, allowing them to remain stable with an excellent long-lasting effect even after dispersal.

The oil phase used for the emulsified composition may be any oleaginous substance which is virtually insoluble in water, and general examples include fats and oils, oil-soluble aromatics, oil-soluble pigments, waxes, insecticides, herbicides, oil-soluble pharmaceuticals and oil-soluble reagents. The emulsifier of the invention, therefore, may be widely used in general bioindustrial products, typical of which are aromatic emulsions, foods such as mayonnaise, dressings and creams, cosmetics such as hand creams, medicines such as ointments and agricultural chemicals such as insecticides.

Embodiments of the invention will now be explained by way of examples, with the understanding that the invention is in no way restricted by the examples. Through the examples, "parts" and "%" are both based on weight.

Preparation of Rhamnogalacturonase

A 100 ml enzyme solution of the commercially available enzyme preparation Pectinex Ultra SP-L was measured out and the buffer solution exchanged with a 20 mM acetate buffer solution (pH 5.0) using an Aidicon ultrafiltration apparatus (with an Amicon PM-10 membrane). The resulting product was used, as the crude enzyme solution, for purification of rhamnogalacturonase to be used for the invention. The chromatograms for each of the steps of the purification are shown in FIGS. 1 to 4.

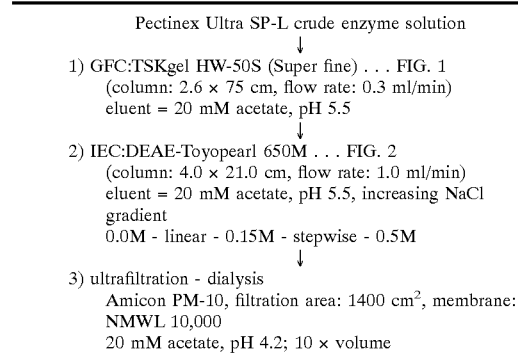

Figure 2:
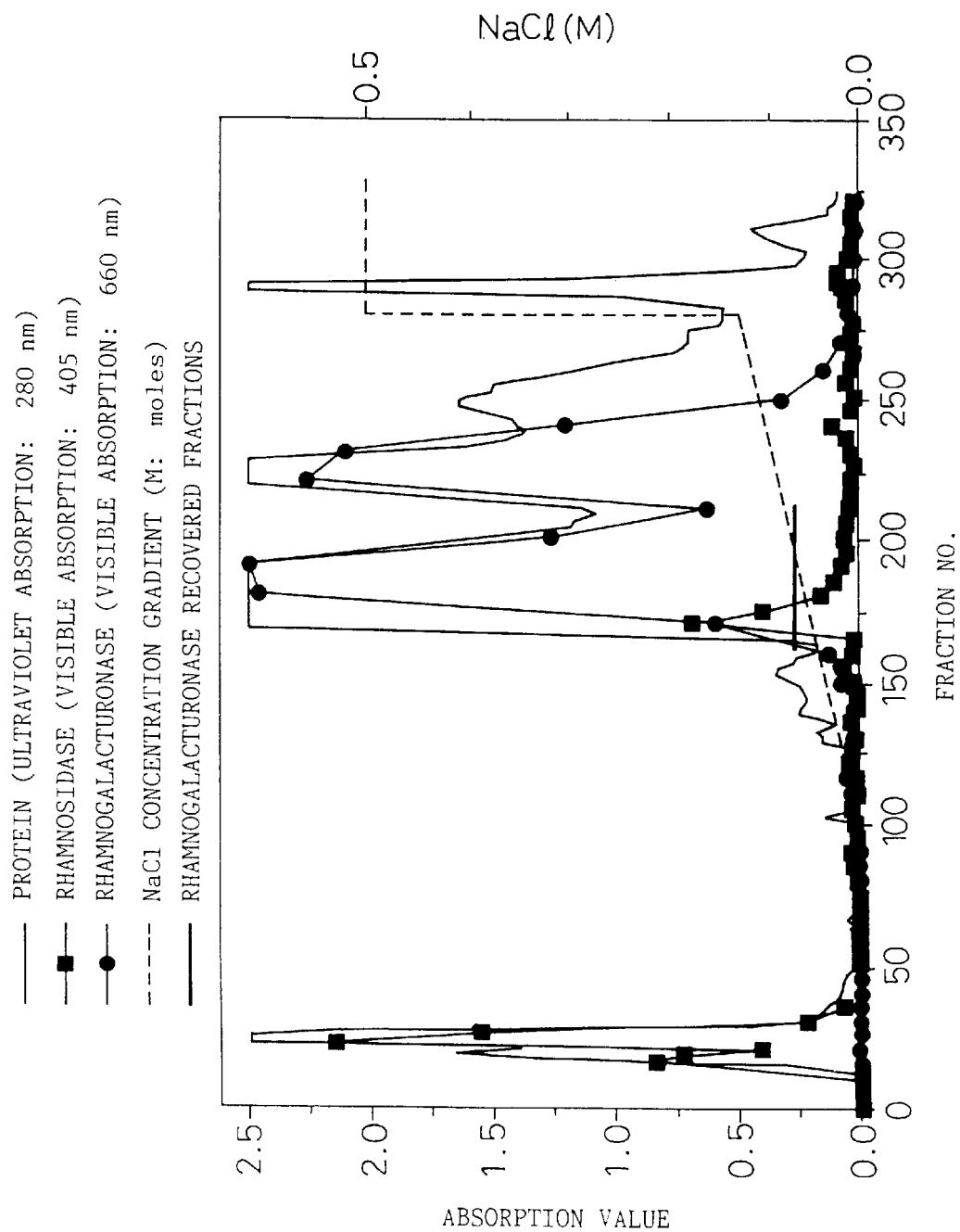
FIG. 2 is a chromatogram from ion-exchange chromatography of a GFC-treated rhamnogalacturonase fraction using a column of IEC:DEAE-Toyopearl 650M (negative ion-exchange chromatography filler, product of Toso Co.).
Figure 3:
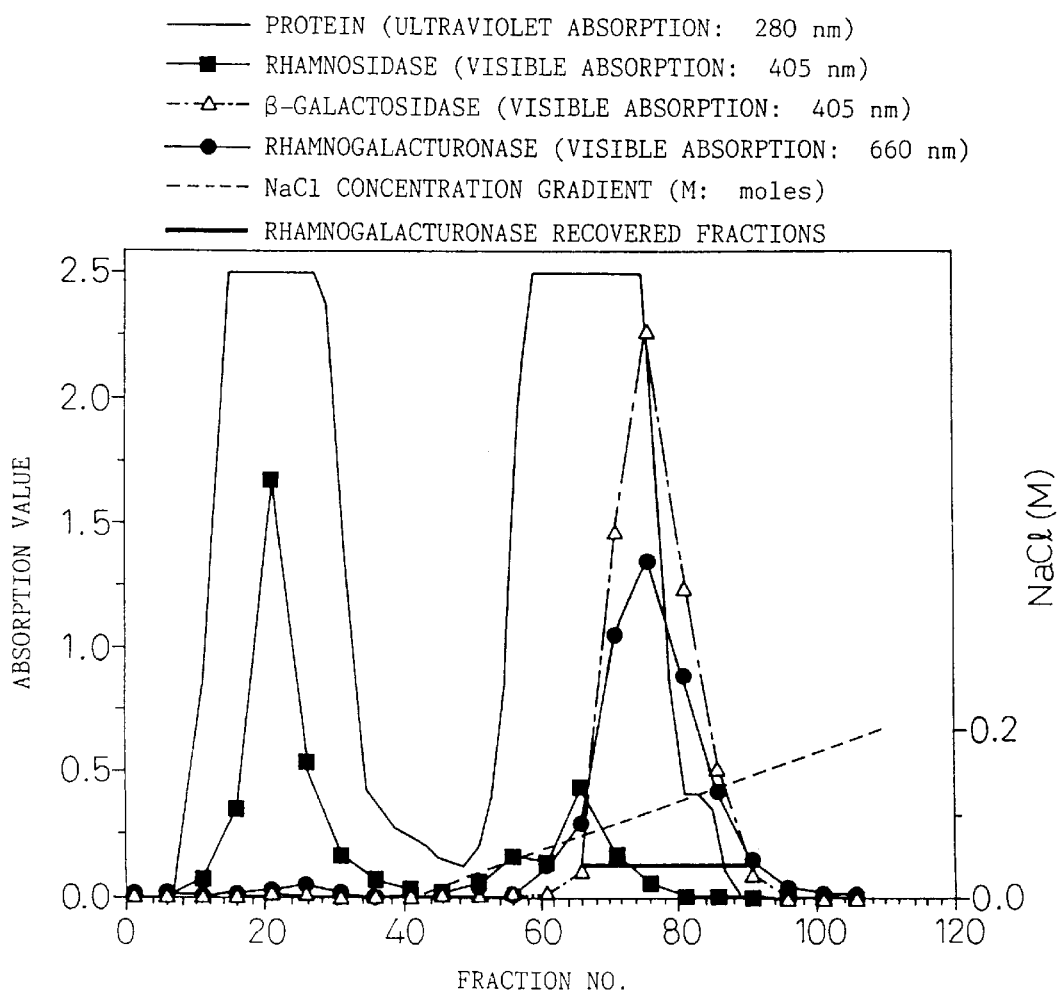
FIG. 3 is a chromatogram from ion-exchange chromatography of a DEAE-Toyopearl 650M-treated rhamnogalacturonase fraction using a column of CM-Toyopearl (positive ion-exchange chromatography filler, product of Toso Co.).

Pectinex Ultra SP-L crude enzyme solution
↓
1) GFC:TSKgel HW-50S (Super fine) . . . FIG. 1
   (column: 2.6 × 75 cm, flow rate: 0.3 ml/min)
   eluent = 20 mM acetate, pH 5.5
   ↓
2) IEC:DEAE-Toyopearl 650M . . . FIG. 2
   (column: 4.0 × 21.0 cm, flow rate: 1.0 ml/min)
   eluent = 20 mM acetate, pH 5.5, increasing NaCl gradient
   0.0M - linear - 0.15M - stepwise - 0.5M
   ↓
3) ultrafiltration - dialysis
   Amicon PM-10, filtration area: 1400 cm$^2$, membrane: NMWL 10,000
   20 mM acetate, pH 4.2; 10 × volume -continued 4) IEC:CM-Toyopearl 650M . . . FIG. 3
   (column: 1.0 × 17.0 cm, flow rate: 0.3 ml/min)
   eluent = 20 mM acetate, pH 4.2, increasing Nacl gradient
   0.0M - linear - 0.2M
   ↓
5) ultrafiltration - dialysis
   Amicon PM-10, filtration area: 1400 cm², membrane: NMWL 10,000
   20 mM acetate, pH 4.2; 10 × volume
   ↓
6) AC:CLRG (crosslinked rhamnogalacturonan) . . . FIG. 4
   (column: 1.5 × 5.0 cm, flow rate: 0.2 ml/min)
   eluent = 10 mM acetate, pH 4.5, increasing Nacl gradient
   0.0M - linear - 0.5M
   ↓
Purified rhamnogalacturonase In 1) above, GFC stands for gel filtration chromatography. The low molecular carbohydrates, salts and browning pigments were completely removed from the crude enzyme solution, while the buffer solution was exchanged in step 2) for adsorption of the reagent onto the column.

In 2), IEC stands for ion-exchange chromatography. The 0.05–0.07 M NaCl elution fractions were pooled for use as the rhamnogalacturonase fraction.

In 3), the buffer solution was exchanged in preparation for step 4).

In 4), IEC stands for ion-exchange chromatography. The 0.09–0.12 M NaCl elution fractions were pooled for use as the rhamnogalacturonase fraction.

In 5), the buffer solution was exchanged in preparation for step 6).

In 6), AC stands for affinity chromatography and CLRG stands for crosslinked rhamnogalacturonan. The affinity column was prepared according to the method of S. Inoue (affinity support preparation method described in S. Inoue et al., Agric. Biol. Chem., 48 (1984) 764), using water-soluble soybean hemicellulose as the base material. Treatment with this column resulted in complete separation and removal of the B-galactosidase present in admixture with the rhamnogalacturonase. The 0.22–0.30 M NaCl elution fractions were pooled for use as the rhamnogalacturonase fraction.

Upon investigating the various properties of the purified rhamnogalacturonase by the methods described above, the optimum pH was found to be in the region of 4.5–5.0. In regard to the pH stability, the residual activity was measured after treatment at 35° C. for 2 hours at different pH levels, and it was found that 80% or more activity was retained in a pH range of 3.5–7.5. The optimum temperature was in a high range of 50–60° C., and 80% or more residual activity was exhibited in a temperature range of 20–45° C. The molecular weight was found to be 60,000 by SDS-PAGE analysis, and the isoelectric point was 4.90. These analyses suggested that the enzyme was identical to the rhamnogalacturonase described in Japanese Patent Publication Inspection No. 6-506831.

The rhamnogalacturonase to be used for the invention is preferably enzymatically pure. The prepared rhamnogalacturonase was therefore analyzed for copresence of pectinase and hemicellulase, giving the results shown below. These results confirmed the virtual absence of all enzyme activity except for that of rhamnogalacturonase. The enzyme activity value of the enzyme in terms of protein was 25 units/mg. The activity value of 20 units/mg or greater was also confirmed to be effective.

Analysis results

| Enzyme name | | Activity (units/ml) |
|---|---|---|
| Pectinase[1] | | 0.0 |
| Hemicellulase[2] | α-glucosidase | 0.0 |
| | β-glucosidase | 0.021 |
| | α-mannosidase | 0.0 |
| | α-xylosidase | 0.0 |
| | β-xylosidase | 0.0 |
| | α-fucosidase | 0.0 |
| | α-galactosidase | 0.0 |
| | β-galactosidase | 0.036 |
| | α-arabinosidase | 0.011 |
| | α-rhamnosidase | 0.0 |
| Rhamnogalacturonase[3] | | 135.0 |

[1] After decomposition at 35° C. for 2 hours using commercially available pectin as the substrate (0.1 wt % in reaction solution), the increase in reducing power was measured by the Somogyi-Nelson method.
[2] After decomposition at 35° C. for 30 minutes using the commercially available synthetic substrate p-nitrophenyl-glycoside, the amount of free phenol was quantified in terms of absorption at 405 nm. One unit was defined as the amount of enzyme required to free phenol to an absorption value of 1.0 in terms of the absorption at 405 nm per one minute of reaction time.
[3] Rhamnogalacturonan was prepared from commercially available pectin according to the method of J. A. Devries, F. M. Rombouts, A. G. J. Voragen and W. Pilink, Carbohydr. Res., 2 (1982) 25–33, and this was used as the substrate for measurement of activity by the method of 1) above.

Preparation of Water-soluble Soybean Hemicellulose

To raw okara obtained from production of separated soybean protein there was added a 2-fold amount of water, and after adjustment to pH 4.5 with hydrochloric acid, the mixture was heated at 120° C. for 1.0 hour and the water-soluble soybean hemicellulose was extracted. After extraction, the mixture was centrifuged (5000 G×10 min) and the water-soluble fraction containing primarily water-soluble soybean hemicellulose was separated. Sodium hydroxide was added to the aqueous solution containing the water-soluble soybean hemicellulose which was obtained in this manner, and the pH was adjusted to 12. The mixture was then heated at 70° C. for 30 minutes. The precipitate resulting from heating was removed, and the solution was neutralized with hydrochloric acid (pH 7). The resulting water-soluble soybean hemicellulose solution was desalted by dialysis, and after treatment with an activated carbon column, it was dried to prepare water-soluble soybean hemicellulose (A).

EXAMPLE 1

The water-soluble soybean hemicellulose (A) was dissolved in a 20 mM acetate buffer solution (pH 5.0) to 5% concentration, and the purified rhamnogalacturonase prepared earlier was added in an amount of ⅟₁₀ of the water-soluble soybean hemicellulose for decomposition at 40° C. for 24 hours while stirring. After the enzyme decomposition, the mixture was subjected to heat treatment at 90° C. for 5 minutes for enzyme deactivation and then centrifuged (5000 G×10 min) to separate the water-soluble fraction containing the enzyme-decomposed water-soluble soybean hemicellulose. The aqueous solution of enzyme-decomposed water-soluble soybean hemicellulose obtained in this manner was transferred to a cellophane tube and dialyzed for desalting, and was then dried to obtain the enzyme-decomposed water-soluble soybean hemicellulose (B).

Ten parts of enzyme-decomposed water-soluble soybean hemicellulose (B) obtained above was dissolved in 80 parts of water, a mixed oil comprising 6.5 parts of SAIB (sucrose acetic isobutyric ester) and 3.5 parts of orange oil was dispersed in the solution to a volume of 100 parts, and the pH was adjusted to 4.0 with a 50% citric acid solution, after which the dispersion was emulsified with a homogenizer (300 kgf/cm$^2$). The emulsion was of low viscosity and therefore of satisfactory handleability, while despite the lack of addition of other emulsifiers the emulsified state was stably maintained, undergoing no change even after cold storage for a period of 3 months, and therefore the emulsion was extremely stable. Next, 8.7% sucrose and 0.3% citric acid were dissolved in 100 ml of water, after which 0.1% of the previous emulsion was also added, to obtain an orange-like soft drink. Air was bubbled through the drink at a flow rate of 2.2 ml/min and the turbidity before and after bubbling was measured at an absorbance of 620 nm, upon which the bubbling resistance, defined as the ratio of the turbidity after bubbling with respect to the turbidity before bubbling, was determined to be 88.3%. A higher bubbling resistance indicates higher emulsion stability of diluted solutions. Even after a lapse of 3 months, the suspension was stable without any observable change in the emulsified particles.

When the same procedure was carried out using water-soluble soybean hemicellulose (A) as a control, the bubbling resistance was slightly inferior at 78.5%, while the emulsified state was also better when the water-soluble soybean hemicellulose (B) was used.

COMPARATIVE EXAMPLE 1

The water-soluble soybean hemicellulose (A) was dissolved in a 20 mM acetate buffer solution (pH 5.0) to 5% concentration, and the rhamnogalacturonase-containing crude enzyme solution Pectinex Ultra SP-L (enzyme activity value of 0.1 units/mg in terms of protein) was added in an amount of 1/10 of the water-soluble soybean hemicellulose for decomposition at 40° C. for 6 hours while stirring. After the enzyme decomposition, the mixture was subjected to heat treatment at 90° C. for 5 minutes for enzyme deactivation and then centrifuged (5000 G×10 min) to separate the water-soluble fraction containing the enzyme-decomposed water-soluble soybean hemicellulose. The aqueous solution of enzyme-decomposed water-soluble soybean hemicellulose obtained in this manner was transferred to a cellophane tube and dialyzed for desalting, and was then dried to obtain enzyme-decomposed water-soluble soybean hemicellulose (C).

An aromatic emulsion sample was prepared in exactly the same manner as Example 1, except that the enzyme-decomposed water-soluble soybean hemicellulose (C) obtained above was used instead of the water-soluble soybean hemicellulose (B) in Example 1, and although the emulsion was of low viscosity and therefore of satisfactory handleability, the emulsion particles aggregated and the bubbling resistance was as low as 23.7%, resulting in an unsatisfactory aromatic emulsion.

COMPARATIVE EXAMPLE 2

The water-soluble soybean hemicellulose (A) was dissolved in a 20 mM acetate buffer solution (pH 5.0) to 5% concentration, and the rhamnogalacturonase-containing crude enzyme solution Pectinex Ultra SP-L was added in amount of 1/10 of the water-soluble soybean hemicellulose for decomposition at 40° C. for 24 hours while stirring. After the enzyme decomposition, the mixture was subjected to heat treatment at 90° C. for 5 minutes for enzyme deactivation and then centrifuged (5000 G×10 min) to separate the water-soluble fraction containing the enzyme-decomposed water-soluble soybean hemicellulose. The aqueous solution of enzyme-decomposed water-soluble soybean hemicellulose obtained in this manner was transferred to a cellophane tube and dialyzed for desalting, and was then dried to obtain enzyme-decomposed water-soluble soybean hemicellulose (D).

An aromatic emulsion sample was prepared in exactly the same manner as Example 1, except that the water-soluble soybean hemicellulose (D) obtained above was used instead of the water-soluble soybean hemicellulose (B) in Example 1, and although the emulsion was of low viscosity and therefore of satisfactory handleability, the emulsion particles aggregated and the bubbling resistance was as low as 25.4%, resulting in an unsatisfactory aromatic emulsion.

The composition ratios for water-soluble soybean hemicelluloses (A) to (D) are summarized below.

| Composition ratios of water-soluble soybean hemicelluloses (wt %) | | | | |
|---|---|---|---|---|
| | (A) | (B) | (C) | (D) |
| Water | 5.4 | 9.7 | 9.3 | 8.4 |
| Crude protein | 9.1 | 8.4 | 7.5 | 4.1 |
| Crude ash content | 6.3 | 3.7 | 3.5 | 2.6 |
| Polysaccharides | 79.0 | 78.1 | 79.6 | 84.9 |
| Average molecular weight | 207,000 | 128,000 | 51,000 | 13,000 |
| Viscosity[1] | 56.8 | 27.1 | 10.3 | 4.2 |

[1]Viscosity: cps, 10% aqueous solution

The enzyme-decomposed water-soluble soybean hemicelluloses (B), (C) and (D) of the invention were of lower average molecular weight than the conventional non-enzyme-decomposed water-soluble soybean hemicellulose (A), thus possessing the characteristic of low viscosity. The water-soluble soybean hemicelluloses (C) and (D) underwent degradation of the sugar chains and proteins of the water-soluble soybean hemicellulose by the action of pectinase, hemicellulase and protease in the enzyme solution, and were therefore of even lower molecular weight and lower viscosity than the water-soluble soybean hemicellulose (B).

The sugar compositions of the water-soluble soybean hemicelluloses (A) to (D) were then analyzed by the following method. Uronic acid was measured by the Blumenkrantz method, and the neutral sugars were measured by the GLC method after alditol acetation. The results were as follows.

| Sugar compositions of water-soluble soybean hemicelluloses (wt %) | | | | |
|---|---|---|---|---|
| | (A) | (B) | (C) | (D) |
| Galacturonic acid | 17.6 | 12.5 | 19.6 | 29.8 |
| Rhamnose | 2.6 | 10.8 | 16.3 | 22.9 |
| Fucose | 1.9 | 1.3 | 2.4 | 0.0 |
| Arabinose | 20.5 | 19.7 | 14.8 | 8.5 |
| Galactose | 49.9 | 47.3 | 28.9 | 12.1 |
| Xylose | 6.4 | 6.8 | 10.4 | 12.4 |
| Glucose | 1.1 | 1.6 | 7.6 | 14.3 |

COMPARATIVE EXAMPLE 3

An aromatic emulsion sample was prepared in exactly the same manner as Example 1, except that gum arabic was used instead of the water-soluble soybean hemicellulose (B) in Example 1, and the bubbling resistance was as low as 45.6%, while separation was observed after only one month.

COMPARATIVE EXAMPLE 4

An aromatic emulsion sample was prepared in exactly the same manner as Example 1, except that processed starch (Purity Gum, product of Oji National, KK.)-was used instead of the water-soluble soybean hemicellulose (B) in Example 1, and the bubbling resistance was as low as 35.6%, while separated sedimentation and gelation were observed after only one month.

The emulsified states of each of the above-mentioned aromatic emulsions and their orange-like soft drinks were observed after storage at 5° C. for 30 days. The results were as follows.

|  | Emulsified state[1] | Aromatic emulsion particle size (day 0)[2] | Orange-like soft drink Emulsified state[1] | Aroma[1] | Bubbling resistance (%)[3] |
|---|---|---|---|---|---|
| Control | ○ | 0.6(0.5) | ○ | ○ | 78.5 |
| Example 1 | ⊚ | 0.4(0.4)– | ⊚ | ⊚ | 88.3 |
| Comp.Ex. 1 | x | (4.6) | — | — | 23.7 |
| Comp.Ex. 2 | x | –(12.5) | — | — | 25.4 |
| Comp.Ex. 3 | Δ | 2.3(0.7) | ○ | ○ | 45.6 |
| Comp.Ex. 4 | x | 2.3(0.7) | Δ | ○ | 35.6 |

[1]⊚ = very satisfactory; ○ = satisfactory; Δ = somewhat poor; x = poor; – = unmeasurable
[2]Measured with a laser diffraction-type particle-size distribution measuring apparatus (LA-500, product of HORIBA Co.). Values in parentheses (at day 0 of storage) represent the particle sizes immediately after preparation of the aromatic emulsions. Units = $\mu$m.
[3]Larger bubbling resistance values represent higher emulsion stability when stored as diluted solutions.

As shown above, for decomposition of water-soluble soybean hemicellulose with rhamnogalacturonase, using a crude enzyme with an enzyme activity value of 0.1 unit/mg in terms of protein decomposed both the hemicellulose and protein, thus resulting in an impaired emulsifying property. However, when water-soluble soybean hemicelluloses were decomposed using rhamnogalacturonase purified from the crude enzyme solution with an enzyme activity value of 25 units/mg in terms of protein, the decomposition products exhibited emulsifying properties greater than that of non-enzyme-decomposed water-soluble soybean hemicellulose. The effect of the emulsifying property was satisfactory even with a decomposition product obtained by decomposing the water-soluble soybean hemicellulose to an enzyme activity value of 20 units/mg in terms of the protein. Thus by using decomposition products from decomposition of water-soluble soybean hemicellulose with purified rhamnogalacturonase having an enzyme activity value of at least 20 units/mg, and preferably 25 units/mg of protein, it is possible to prepare aromatic emulsions with low viscosity and satisfactory emulsifying stability, giving stable emulsifying agents even when used in beverages. In addition, the enzyme-decomposed water-soluble soybean hemicellulose (B) was superior even to the similarly low viscosity emulsifying agents gum arabic and processed starch in terms of both emulsifying property and emulsion stability.

EXAMPLE 2

Thirty parts of water-soluble soybean hemicellulose (B) obtained above was dissolved in 30 parts of water, a mixed oil comprising 28.5 parts of SAIB (sucrose acetic isobutyric ester) and 11.5 parts of orange oil was dispersed in the solution to a volume of 100 parts, and the pH was adjusted to 4.0 with a 50% citric acid solution, after which the dispersion was emulsified with a homogenizer (300 kgf/cm$^2$). The emulsion was of low viscosity, despite the high concentration of water-soluble soybean hemicellulose (B), and therefore had satisfactory handleability, while the emulsified state was stably maintained without addition of other emulsifiers, remaining extremely stable even after cold storage for a period of 3 months. Next, 120 parts of sucrose and 2 parts of citric acid were dissolved in 880 parts of water, after which 1 part of the previous emulsion was also added to obtain an orange-like soft drink. The bubbling resistance of the beverage was as high as 87.4%, remaining completely stable even after a lapse of 3 months. When the same procedure was carried out using non-enzyme-decomposed water-soluble soybean hemicellulose (A) as a control, the handleability was slightly poorer because of a higher viscosity and the bubbling resistance was slightly inferior at 78.7%, while the emulsified state was also better when the water-soluble soybean hemicellulose (B) was used.

COMPARATIVE EXAMPLE 5

An aromatic emulsion sample was prepared in exactly the same manner as Example 2, except that gum arabic was used instead of the water-soluble soybean hemicellulose (B) in Example 2 and, although the handleability was satisfactory because of a low viscosity, the emulsifying property was inferior and separation was observed after only one month. The bubbling resistance was 74.6%.

COMPARATIVE EXAMPLE 6

An aromatic emulsion sample was prepared in exactly the same manner as Example 2, except that processed starch (Purity Gum, product of Oji National, KK.) was used instead of the water-soluble soybean hemicellulose (B) in Example 2, and although the handleability was satisfactory because of a low viscosity, aging of the starch resulting in separated sedimentation and gelation which were already observed after 2 weeks.

The emulsified states of each of the above-mentioned aromatic emulsions and their orange-like soft drinks were observed after storage at 5° C. for 30 days. The results were as follows.

|  | Emulsified state[1] | Aromatic emulsion particle size (day 0)[2] | Orange-like soft drink Emulsified state[1] | Aroma[1] | Bubbling resistance (%)[3] |
|---|---|---|---|---|---|
| Control | ○ | 0.9(0.5) | ○ | ○ | 78.7 |
| Example 2 | ⊚ | 0.5(0.4) | ⊚ | ⊚ | 87.4 |
| Comp.Ex. 5 | ○ | 0.9(0.6) | ○ | ○ | 74.6 |
| Comp.Ex. 6 | x | 17.8(0.9) | x | Δ | — |

[1]⊚ = very satisfactory; ○ = satisfactory; Δ = somewhat poor; x = poor; – = unmeasurable
[2]Measured with a laser diffraction-type particle-size distribution measuring apparatus (LA-500, product of HORIBA Co.). Values in parentheses (at day 0 of storage) represent the particle sizes immediately after preparation of the aromatic emulsions. Units = $\mu$m.
[3]Larger bubbling resistance values represent higher emulsion stability when stored as diluted solutions.

EXAMPLE 3

Into 40 parts of water and 18 parts of brewed sake there were added and thoroughly dissolved 3.6 parts of sugar, 3 parts of common salt, 0.3 part of sodium L-glutamate and 10 parts of enzyme-decomposed water-soluble soybean hemicellulose (B). After gradually adding 15 parts of salad oil and using a homomixer for pre-emulsification, the mixture was emulsified with a homogenizer (400 kgf/cm$^2$) to obtain an emulsified salad dressing with low viscosity and good taste and texture.

COMPARATIVE EXAMPLE 17

An emulsified dressing sample was prepared in exactly the same manner as Example 3, except that instead of the enzyme-decomposed water-soluble soybean hemicellulose (B) in Example 3, xanthan gum was used at 0.4% and water was supplied for the remaining portion; however, the dressing was of very high viscosity.

EXAMPLE 4

Four parts of enzyme-decomposed water-soluble soybean hemicellulose (B) was dissolved in 75 parts of water. After then adding 20 parts of purified coconut oil-containing 0.1 part of commercially available milk flavoring (Milk FT-013, product of Takasago Perfumery Co., KK.) at 70° C., the mixture was pre-emulsified with a homomixer. A high-pressure homogenizer was then used for emulsification (500 kgf/cm$^2$) to obtain a whitener for coffee. The whitener maintained a stable emulsified state, which remained stable even after storage for one month. Upon addition thereof to coffee (80° C., pH 5.3) containing 5% sugar, absolutely no feathering occurred and the coffee had a mild flavor.

EXAMPLE 5

Five parts of enzyme-decomposed water-soluble soybean hemicellulose (B) was dissolved in 60 parts of water, and then 11 parts of propylene glycol, 0.5 part of triethanolamine, 0.5 part of an oleaginous aromatic and a suitable amount of a preservative were added to make an aqueous phase. Separately, 5 parts of stearic acid, 2 parts of bees wax, 6 parts of cetanol, 10 parts of squalene and 1 part of lanolin were mixed to prepare an oil phase which was then added to the above-mentioned aqueous phase and pre-emulsified with a homomixer. The pre-emulsion was then emulsified with a nanomizer (750 kgf/cm$^2$). The emulsion maintained a stable emulsified state, which remained stable even after storage for 6 months. When applied to hands as a hand cream, it had a satisfactory fresh feel and maintained a soft moistness.

Industrial Applicability

As explained above, emulsifiers obtained according to the process of the invention have low viscosity and excellent handleability, and therefore when these emulsifiers are used to prepare aromatic emulsions, the emulsions are stabilized over long periods even in the form of final beverage products, and when used in mayonnaise, dressings and the like, they give very smooth emulsified dressings without the high viscosity characteristic of xanthan gum. The present invention also provides various other effects, as it allows production of creams which are highly resistant to pH changes and can also be effectively utilized for emulsification of cosmetics and agricultural chemicals.

We claim:

1. A process for producing an emulsifier, which comprises hydrolysis of water-soluble hemicellulose with purified rhamnogalacturonase, wherein the purity of the rhamnogalacturonase is such as to give an enzyme activity value of at least 20 units/mg.

2. The production process of claim 1, wherein the water-soluble hemicellulose is derived from soybeans.

* * * * *

UNITED STATES PATENT AND TRADEMARK OFFICE
CERTIFICATE OF CORRECTION

PATENT NO.    : 6,015,840
DATED         : January 18, 2000
INVENTOR(S)   : Akihiro Nakamura et al.

Page 1 of 1

It is certified that error appears in the above-identified patent and that said Letters Patent is hereby corrected as shown below:

Column 1,
Line 63, after "obtained" delete "us uch" and insert -- using such --.

Column 2,
Line 66, delete "-" between "and" and "another".

Column 4,
Line 46, delete "Aidicon" and insert -- Amicon --.

Column 5,
Line 5, delete "Nacl" and -- NaCl --.
Line 14, delete "Nacl" and insert "NaCl".

Column 8,
Line 6, after "that the" insert -- enzyme-decomposed --.

Signed and Sealed this

Nineteenth Day of March, 2002

Attest:

JAMES E. ROGAN
Director of the United States Patent and Trademark Office

*Attesting Officer*